United States Patent
Laros, Jr.

[11] Patent Number: 5,928,168
[45] Date of Patent: *Jul. 27, 1999

[54] METHOD AND APPARATUS FOR ESTIMATING AND DISPLAYING FETAL DEVELOPMENT DATA DURING PREGNANCY

[76] Inventor: Russell K. Laros, Jr., 21 Marsh Rd., Tiburon, Calif. 94920-2541

[*] Notice: This patent issued on a continued prosecution application filed under 37 CFR 1.53(d), and is subject to the twenty year patent term provisions of 35 U.S.C. 154(a)(2).

[21] Appl. No.: 08/703,769

[22] Filed: Aug. 27, 1996

[51] Int. Cl.$^6$ ..................................................... A61B 5/103
[52] U.S. Cl. ........................................... 600/588; 600/551
[58] Field of Search ..................................... 128/738, 775

[56] References Cited

U.S. PATENT DOCUMENTS

| | | |
|---|---|---|
| 4,303,996 | 12/1981 | Schmitz . |
| 4,367,527 | 1/1983 | Desjacques ............................. 128/738 |
| 4,698,783 | 10/1987 | Nishimuro et al. . |
| 4,780,839 | 10/1988 | Hiryama . |
| 4,847,760 | 7/1989 | Yagi . |
| 4,853,682 | 8/1989 | Asano et al. . |
| 4,991,159 | 2/1991 | Tomoda et al. . |
| 5,012,229 | 4/1991 | Lennon et al. . |
| 5,097,429 | 3/1992 | Wood et al. . |
| 5,113,380 | 5/1992 | Levine . |
| 5,337,290 | 8/1994 | Ventimiglia et al. . |
| 5,365,494 | 11/1994 | Lynch . |
| 5,443,288 | 8/1995 | Miles .......................................... 283/2 |
| 5,471,438 | 11/1995 | Kobayashi et al. . |
| 5,626,133 | 5/1997 | Johnson et al. .......................... 600/300 |
| 5,636,870 | 6/1997 | Enhorning .................................... 283/2 |

*Primary Examiner*—Cary O'Connor
*Assistant Examiner*—Pamela L. Wingood
*Attorney, Agent, or Firm*—Dorsey & Whitney LLP

[57] ABSTRACT

A method and apparatus for determining and displaying fetal development data during pregnancy which allows a user to instantly view the current status of fetal development based on user defined pregnancy reference data. Pregnancy reference data, including a pregnancy reference date such as the expected due date, is entered by the user and stored in a storage device. Thereafter, whenever the user requests the information concerning the fetus, the apparatus estimates the current status of fetal development using the pregnancy reference data and a look-up table containing various parameters. The apparatus then provides a convenient display of the current status of fetal development. The display may be in the form of current gestation measurements or expected current fetal measurements, such as the expected size and weight of the fetus.

19 Claims, 11 Drawing Sheets

LOOK UP TABLE

| WEEK | DAY | WEIGHT (GRAMS) | LENGTH (CENTIMETERS) | PAGE REFERENCE |
|---|---|---|---|---|
| 0 | 0 | 0.0 | 0 | 3 TO 7 |
| | 1 | 0.5 | 0.2 | 3 TO 7 |
| | 2 | 1.0 | 4 | 3 TO 7 |
| | 3 | 1.5 | | |
| | 303 | | 51.9 | 22 TO 24 |
| | 304 | 3714.3 | 51.9 | 22 TO 24 |
| | 305 | 3705.7 | 52.0 | 22 TO 24 |
| | 306 | 3697.1 | 52.0 | 22 TO 24 |
| | 307 | 3688.6 | 52.0 | 22 TO 24 |
| 44 | 308 | 3680.0 | 52.0 | 22 TO 24 |

*Fig. 8*

METHOD AND APPARATUS FOR ESTIMATING AND DISPLAYING FETAL DEVELOPMENT DATA DURING PREGNANCY

BACKGROUND OF THE INVENTION

This invention is broadly directed to a method and apparatus to store and display pregnancy related data.

1. Field of the Invention

The invention is directed to the health care field and the fields of data storage, calculation, and display. More particularly, the invention relates to the storage and processing of pregnancy related data, and display of up-to-date information concerning fetal development.

2. Description of Related Art

A woman's peace of mind regarding her pregnancy helps maintain her health and the health of the unborn child. Peace of mind can be increased by informing the expectant woman of factual information concerning her current stage of pregnancy and informing her of recent developments of her fetus.

Currently, expectant parents must go through the inconvenience of making an appointment with their physician if they wish to learn of the stage of their fetus' development or need general information concerning pregnancy. This creates some anxiety for the expectant parents as they await feedback from the physician. Additionally, the costs of health care are increased as physicians must perform extra work in retrieving, compiling, and explaining the information sought by the parents.

While there are devices currently available that provide generic data storage, calculation, and retrieval, none address the needs of pregnant women. An example is U.S. Pat. No. 5,113,380, to Levine. This patent is directed to an electronic daytimer. Another patent, U.S. Pat. No. 5,337,290, to Ventimiglia et al., describes a watch that stores and displays personal medical information. Other U.S. patents in the prior art include: U.S. Pat. No. 4,780,839 to Hirayama; U.S. Pat. No. 4,303,996 to Schmitz; U.S. Pat. No. 5,012,229 to Lennon et al.; U.S. Pat. No. 5,365,494 to Lynch; U.S. Pat. No. 5,097,429 to Wood et al.; U.S. Pat. No. 4,853,682 to Asano et al.; U.S. Pat. No. 4,847,760 to Yagi; U.S. Pat. No. 4,698,783 to Nishimuro et al.; and U.S. Pat. No. 4,991,159 to Tomoda et al.

The devices of the prior art work as either generic calculators, electronic schedulers or portable data storage and retrieval devices. The disadvantage of these devices is that they are not specifically geared to address the needs of pregnant women, or any person who wants to know the stage of a fetus' development.

The prior art devices are not pre-programmed to store pregnancy related information, nor to provide fetal development data at the touch of a button. The devices are not convenient and are unable to give a pregnant woman the peace of mind that a device specifically designed for her could provide. The devices in use in the prior art are not tailored for individual women.

The current methods of obtaining pregnancy information require the intervention of a physician, and therefore increases the costs of health care.

What is needed is a device addressed to the specific needs of expectant parents or other interested persons that will allow them to conveniently check on the stage of the fetus' development and on the stage of the expectant mother's pregnancy.

What is needed is to provide the ability to customize this device with information specific to the expectant mother, thereby increasing the accuracy of the device and providing the capability of reusing the device.

What is needed is to decrease the cost of health care by reducing the workload on the obstetrician's office.

SUMMARY OF THE INVENTION

The present invention is a method and apparatus for determining and displaying current information about the stage of a fetus' development during pregnancy. The present invention automatically estimates and displays current information concerning the stage of fetal development based on an expectant woman's pregnancy reference data and the current date. The pregnancy reference data can be as simple as merely the date of the woman's last missed period, or as sophisticated as fetus age based on an ultrasound scan, the fetus' percentile, and the fetus' sex. The present invention also may provide information about the woman's current stage of pregnancy, and may inform her of what changes to expect in her body in the near future.

Additionally, the invention allows for a user to update the pregnancy reference data as more refined information about the expectant woman's pregnancy is gained. The updated pregnancy reference data could be obtained from a physician, or any other source known in the art. The updated pregnancy reference data may be data learned from a prior pregnancy.

The invention described herein is an improvement on the existing types of data storage, calculation and display devices because it specifically addresses the needs and desires of expectant parents or other interested persons. The present invention helps to provide expectant parents with peace of mind by providing them with the opportunity to access current information concerning their fetus' stage of development and of the stage of the expectant mother's pregnancy. This information may be obtained whenever the user wishes, simply be pressing a button. The invention provides pregnancy information efficiently, conveniently, and immediately, enabling users to receive current, timely estimates concerning a fetus between visits to the physician. Further, the invention is preferably embodied in small, portable device, such as a watch, for added convenience and portability.

It is an object of the present invention to provide a method and device for determining and displaying the current status of a fetus development.

It is an object of the present invention to automatically determine and immediately display information regarding the current status of a fetus' development and the current stage of pregnancy based on an expectant woman's pregnancy reference data.

It is an object of the present invention to provide a watch that automatically determines and displays information regarding the current status of fetus development and on the expectant woman's stage of pregnancy based on pregnancy reference data entered by the woman and the current date.

It is an object of the present invention to automatically provide a pregnant woman or expectant father with current, up-to-date information regarding the normal status of fetus development based on the woman's current stage of pregnancy and other parameters.

It is an object of the present invention to provide a portable, compact device that allows interested persons to automatically retrieve the current status of fetus development at a plurality of stages of development during pregnancy.

It is an object of the present invention to provide a customizable device which can be tailored to use data concerning a specific woman, and which can be reused in future pregnancies.

It is an object of the invention to reduce the high cost of health care.

DESCRIPTION OF THE DRAWINGS

FIG. 2b shows a block diagram of the hardware components of the watch embodiment previously shown in FIGS. 1 and 2a.

FIG. 8 shows an exemplary look-up table used during the Determine Parameters routine of FIG. 7.

DESCRIPTION OF THE PREFERRED EMBODIMENT(S)

1. Overview

Figure 1:
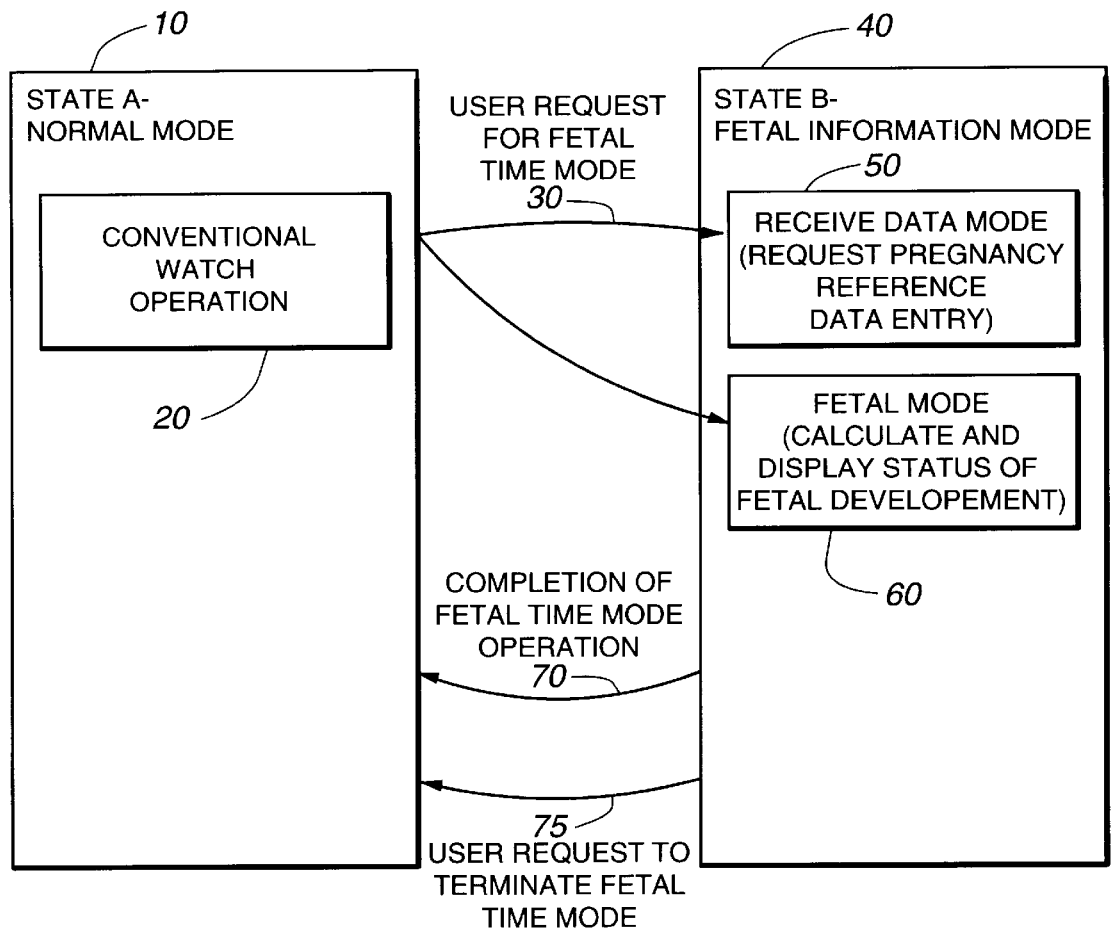
FIG. 1 shows a flowchart depicting the basic functioning of a watch embodiment of the present invention, showing normal mode and Fetal Information mode.

FIG. 1 shows the present invention embodied in a normal wristwatch. FIG. 1 is a flowchart showing the two main modes or states of the present invention: Normal mode 10, including conventional watch operation mode 20, and Fetal Information mode 40, including a Receive Data mode 50 and a Fetal mode 60.

Generally, the invention is in the Normal mode state 10, which in this embodiment consists of functioning as a conventional watch 20. Normal watch functions include setting and displaying the current date, time, etc. In addition, the user may have access to other available, commonly known modes or functions on the watch, such as a calculator mode, a schedule planning mode, etc. Alternatively, if the invention is embodied in an electronic day-timer, the normal mode may be a calendar display. If the invention is embodied in a pager the normal mode may be a receive page mode.

Upon a user request 30, a Fetal Information mode 40 is entered. From the user's standpoint, Fetal Information mode includes two submodes: Receive Data mode 50, and Fetal mode 60. The Receive Data mode 50 includes a request for a pregnancy reference date, such as the date of the last missed menstrual period. The Fetal mode 60 includes the display of information regarding gestational period measurements, such as the fetus' gestational age and how much of the pregnancy term is left. The measurements also include expected fetal measurements, such as the fetus' weight and length. The gestational period measurements are discussed in more detail below in conjunction with FIGS. 3, 4, 5, 6a–6c, and 9a–9d.

Upon completion of Fetal Information mode 70 or, alternatively, upon user request to terminate Fetal Information mode 75, the Normal mode of operation 10 is resumed.

2. Detailed Description of Structure

Figure 2A:
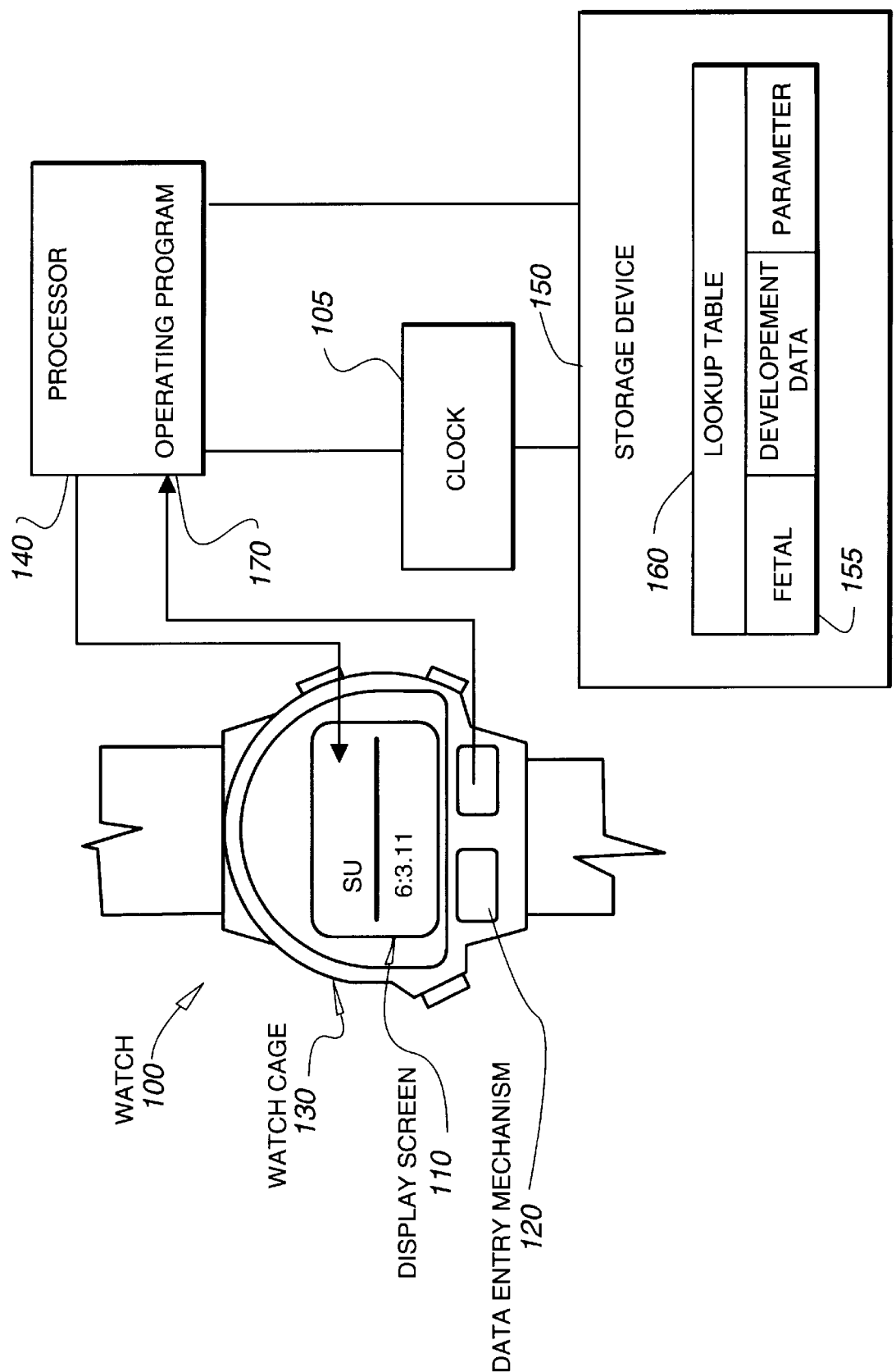
FIG. 2a shows a block diagram of a watch embodiment of the invention.

FIG. 2a shows a block diagram of a preferred system used to realize this invention in the watch embodiment. The watch 100 contains a conventional watch case 130 and a display screen 110, used for protecting the watch and providing a display, respectively. To enter data, a data entry mechanism 120 is provided. This mechanism 120 may be similar to conventional watch setting buttons.

The watch 100 also contains a processor 140, running under an operating program 170. The operating program contains the routines utilized by this invention and described herein. A dock 105 is used to generate time and date information.

A storage device 150 is connected to the processor 140, and provides the processor 140 with information needed to run routines in the operating program 170. A look-up table 105 within the storage device 150 is used to store this information, including fetal development parameter data 155, which is used to calculate the current status of fetal development. Alternatively, a separate storage device may be used for the look-up table.

During Normal mode 10, the watch 100 uses the dock 105 to operate as a conventional watch, and displays conventional watch data on the display screen 110. A user enters a request 30 for Fetal Information mode 40 using the data entry mechanism 120. When in the Receive Data mode 50 of Fetal Information mode 40, the data entry mechanism 120 is used to enter pregnancy reference data. When in Fetal mode 60, the display screen 110 is used to display the current status of fetal development.

In response to entering the Receive Data mode 50, the pregnancy reference data is entered via the data entry mechanism 120. The pregnancy reference data is then processed by the processor 140 prior to storage in the storage device 150. The Receive Data mode executes a Receive Data routine 450, described below with respect to FIG. 5.

Upon receiving a request for the Fetal mode 60 via the data entry mechanism 120, the processor 140, under control of the operating program 170, retrieves the pregnancy reference data from the storage device 150 and preferably, the current date from the clock 105. Alternatively, the current date may be entered as part of the pregnancy reference data.

The processor 140 then determines the relevant fetal development parameter data 140, retrieves it from the storage device 150, and processes the information in order to estimate the current status of fetal development. The current status of fetal development is then displayed on the display screen 110, and Normal mode 10 is resumed.

Figure 2B:
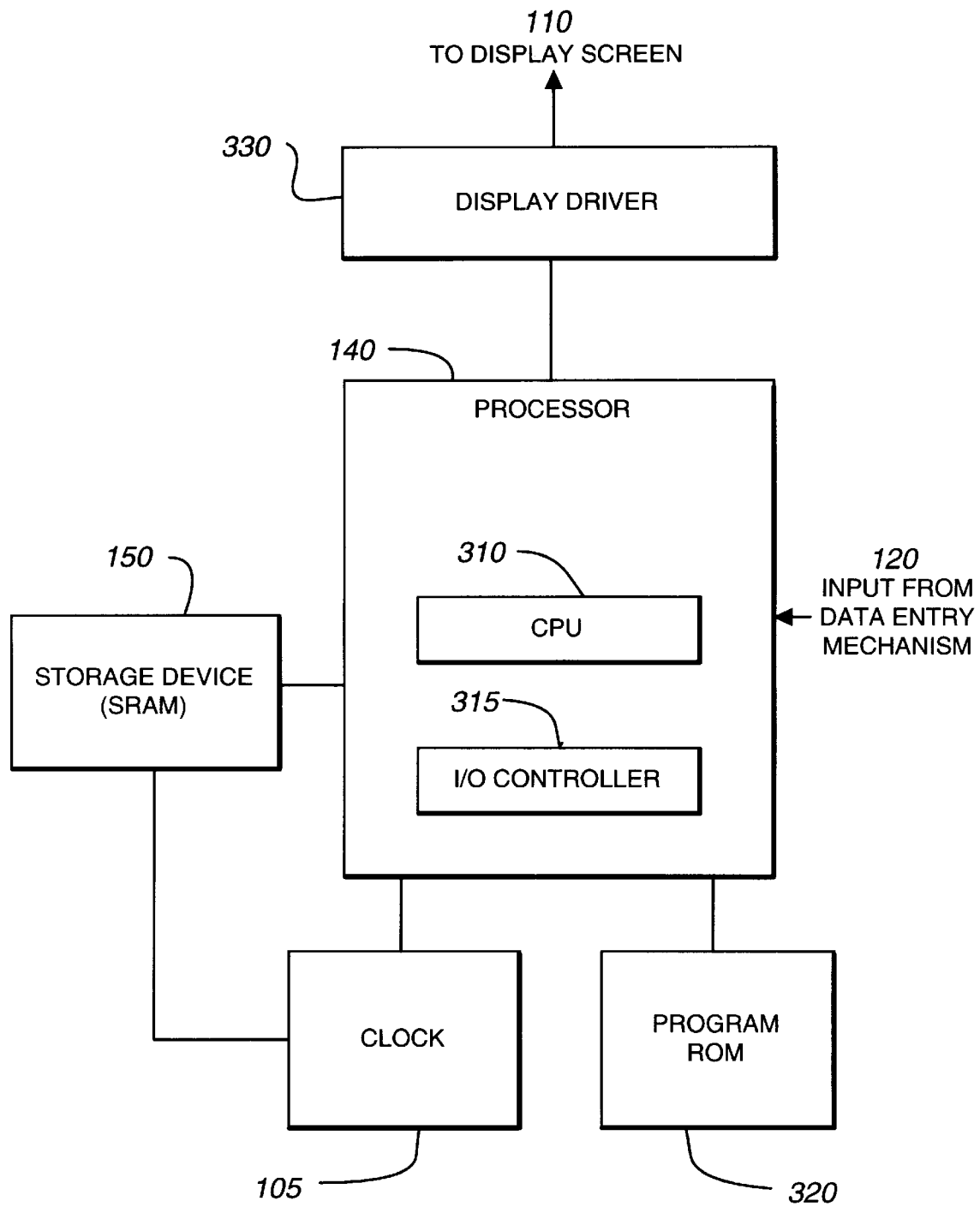

Referring to FIGS. 2a and 2b, the watch case 100 may be formed in a normal wristwatch design, as shown, or other designs including a pendant watch, or a pocket watch. Preferably, the display screen 110 is a standard, alphanumeric LCD display screen, but may also be a gas plasma display or any other type. The data entry mechanism 120 may be a numeric keypad or two button mechanism that is located on the watch and which allows the user to toggle between Fetal Information mode 40 (FIG. 1) and Normal mode 10 (FIG. 1) operation, to enter pregnancy reference data, and to scroll through the current status of fetal development screens, if necessary.

The processor 140 is preferably an ASIC, which is a design known to one of ordinary skill in the art. As shown in FIG. 2b, the processor 140 has core processor or CPU 310 and an I/O controller 315, which are controlled by an operating program ROM 320. A display driver 330, is connected to the CPU to drive the display screen 110.

The storage device 150 for the pregnancy reference data should have a safe, non-volatile form, and preferably takes the form of battery backed up static random access memory (SRAM). A separate storage device, such as a ROM, may be used for the look-up table 160.

While this embodiment describes the invention in combination with a watch, alternative embodiments include combining the invention with any computer or electronic device having an input to receive pregnancy reference data, a processor, and a display or printer to show the user the current status of fetal development. Examples include personal electronic schedulers, calculators and pagers.

Figure 2C:
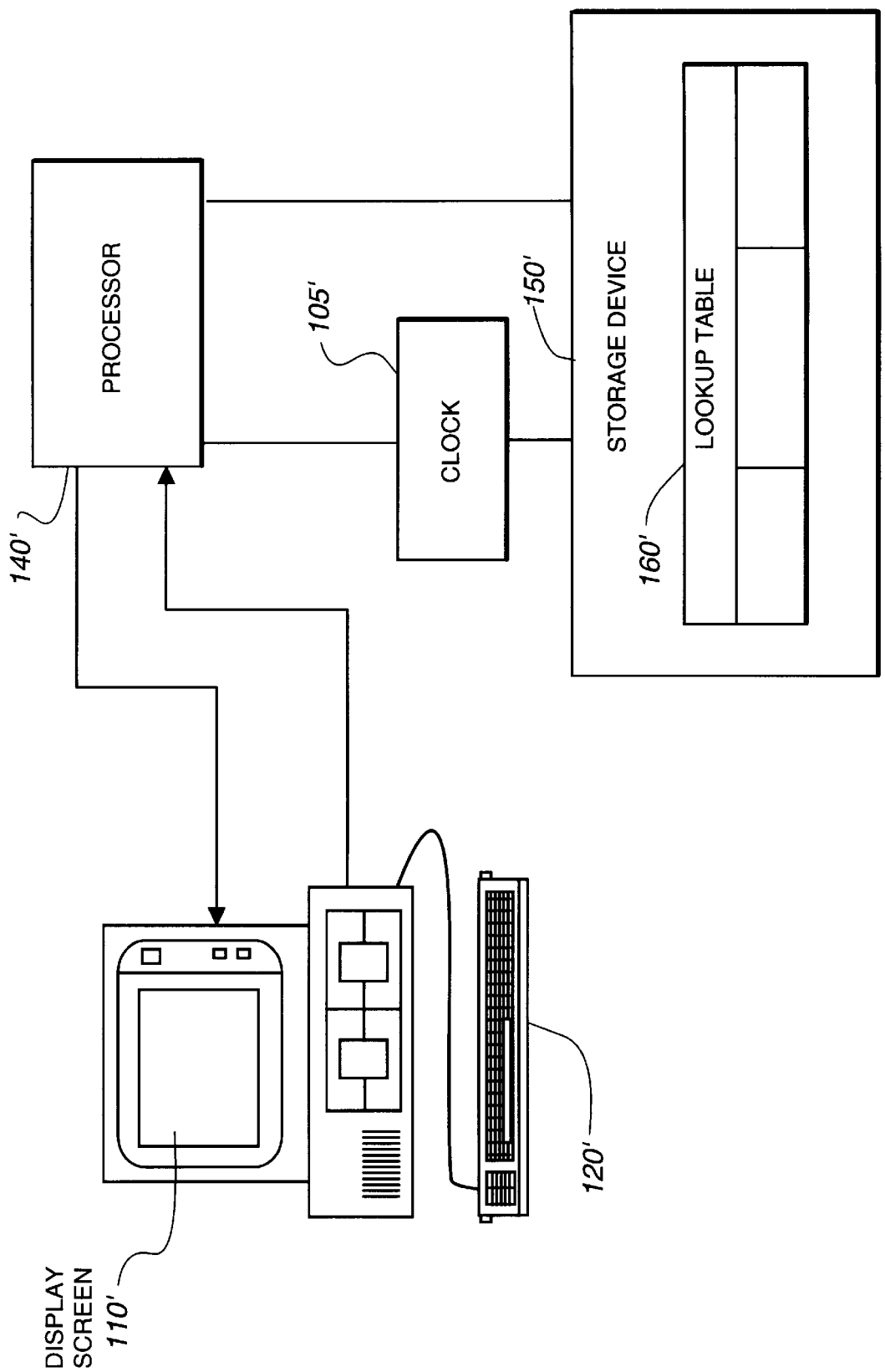
FIG. 2c shows a block diagram of a computer embodiment of the invention.

For example, FIG. 2c shows an embodiment where the invention is implemented in a computer system. Elements having a common function with the elements shown in FIG. 1 are numbered as the primes (') of the reference numbers described with respect to FIG. 1.

The computer embodiment of FIG. 2c uses a display screen 110' and keyboard 120' to show pregnancy information to the user and to allow the user to input data, respectively. The processor 140', clock 105', storage device 150' and look-up table 160' function in the manner previously described with respect to FIG. 1.

Figure 3:
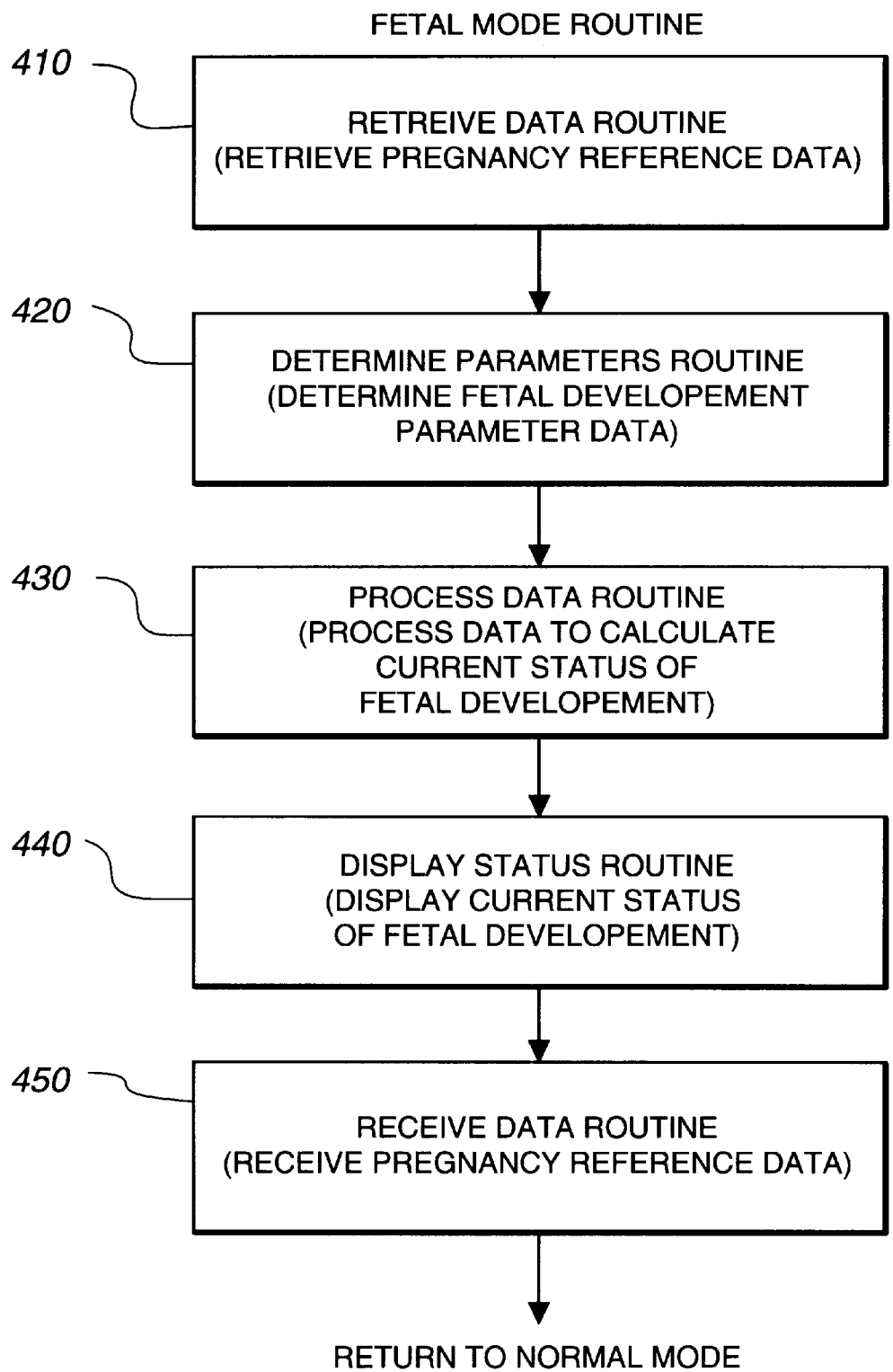
FIG. 3 shows a flowchart of a Fetal mode software routine.

Pregnancy reference data is entered via the keyboard 120', processed through the processor 140', and stored in the storage device 150'. Using the stored data, the look-up table 160' and the clock 105', the processor processes the request for the current status of fetal development. The result is displayed on the computer screen 3. Detailed Description of Operation and Software Routines FIG. 3 shows a flow chart of a software routine used during Fetal mode 60 shown in FIG. 1.

Upon receiving a user request for Fetal mode 60, the Fetal Mode routine executes the Retrieve Data routine 410 to retrieve the pregnancy reference data. Using the retrieved pregnancy reference data, the Determine Parameters routine 420 determines the corresponding fetal development parameter data. The Process Data routine 430 then processes the pregnancy reference data and fetal development parameter data to calculate the current status of fetal development. The Display Status routine 440 then causes a display of the current status of fetal development on the display screen 440.

Finally, before returning 70 to Normal mode 10 (FIG. 1), the Fetal mode routine 60 gives the user an opportunity to view any stored pregnancy reference data, and update the data if desired. This is performed by the Receive Data routine 450.

The Receive Data mode 50, shown in FIG. 1, is also implemented by the Retrieve Data routine 450. While the flow chart of FIG. 3 shows each step in sequential order, sequential order is not necessary. For example, the user may select the Receive Data routine 450 at some point without previously going through the Display Status routine 440. Alternatively if the pregnancy reference data is already stored, the user may choose to only view the current status of fetal development and not review the entered pregnancy reference data. Each of these routines, and other alternative embodiments of the program, are discussed in more detail below with reference to FIGS. 4, 5, 6a–6c, 7, 8, and 9a–9d.

Figure 4:
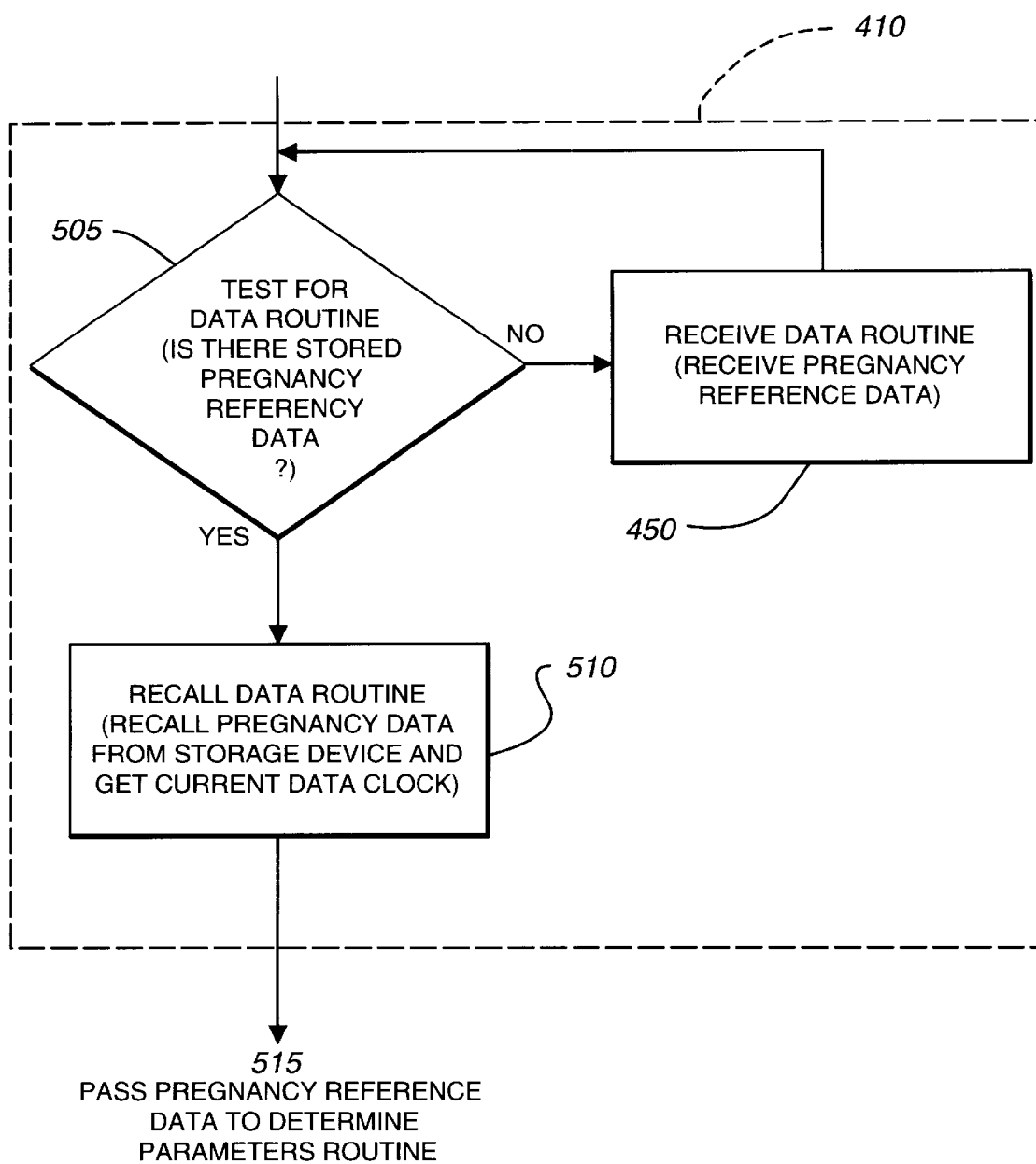
FIG. 4 shows a flowchart of a Retrieve Data software routine.

FIG. 4 shows a more detailed flowchart for the Retrieve Data routine 410, shown in FIG. 3. Upon receiving a user request to access Fetal mode 60 (FIG. 1), the routine checks to see if there is any pregnancy reference data available at Test for Data routine 505.

Ordinarily, the Retrieve Data routine 410 requires that the pregnancy reference data include a pregnancy reference date, and a current date, preferably retrieved from the clock. Alternatively, the current date may be retrieved via the Receive Data routine 450, described below with respect to FIG. 5.

If at least a pregnancy reference date and current date are available, the Recall Data routine 510 recalls all of the pregnancy reference data available, including the current date from the dock or from user entry, and passes it at step 515 to the Determine Parameters routine 420 (FIG. 3).

If the Test for Data routine 505 within the Retrieve Data routine 410 determines that there is insufficient pregnancy reference data available, the Receive Data routine 450 is called. The Retrieve Data routine 410 loops to Receive Data routine 450 until sufficient pregnancy reference data is obtained. The Retrieve Data routine 410 then proceeds, at step 515, to the Determine Parameters routine 420.

Figure 5:
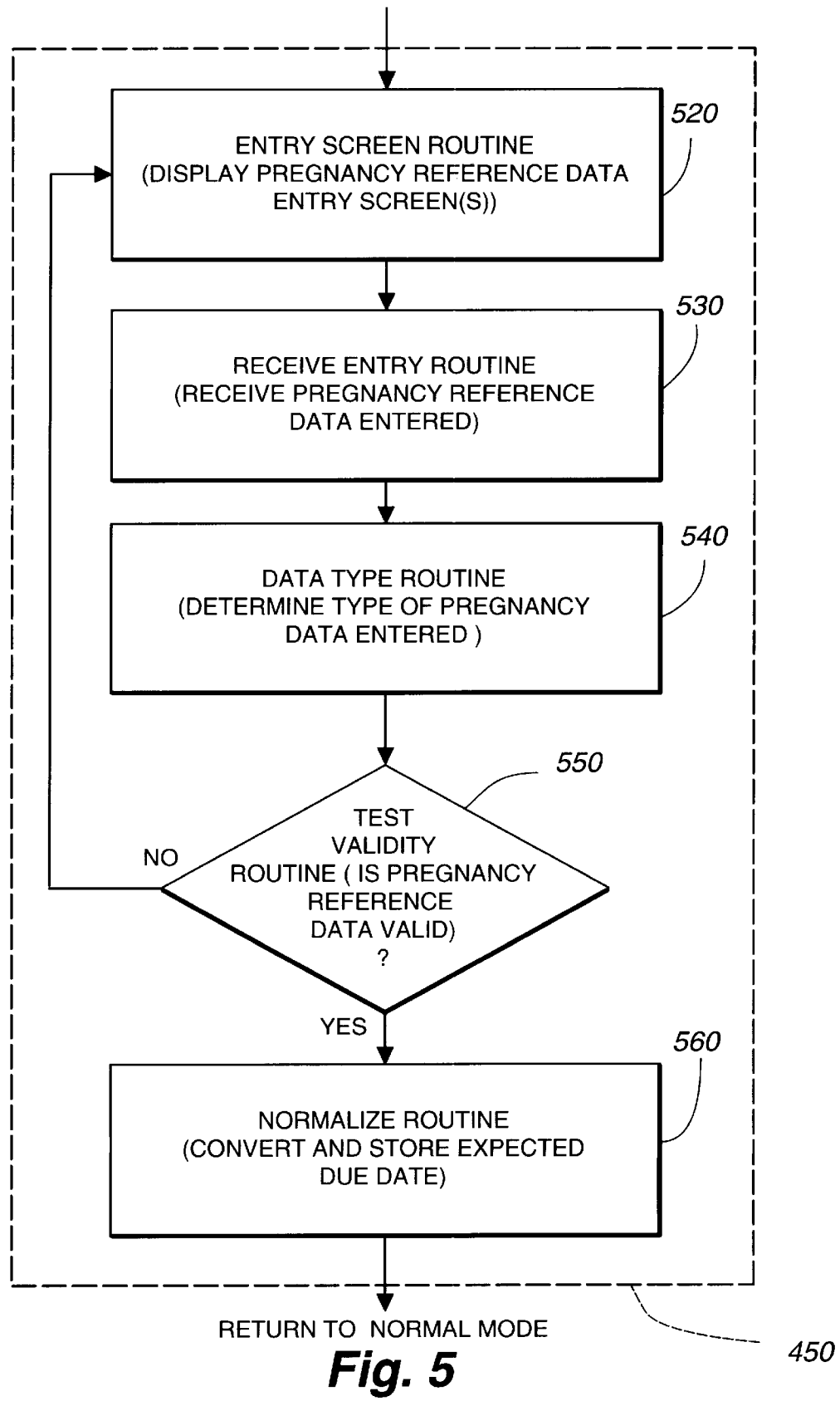
FIG. 5 shows a flowchart of the Receive Data software routine.

FIG. 5 shows a more detailed depiction of the routines involved in the Receive Data routine 450. The Receive Data routine 450 may also be called directly by the user to update stored information by accessing Receive Data mode 50, as shown in FIG. 1.

Figure 6A:
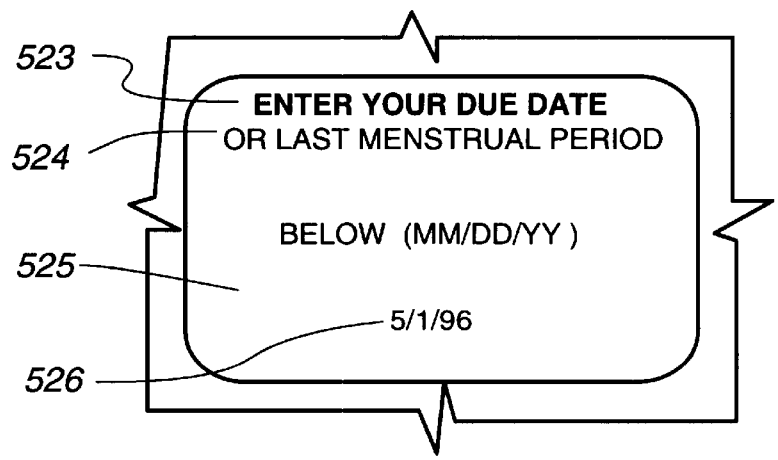
FIGS. 6a–6c show exemplary data entry screens used during the Receive Data routine of FIG. 5.
Figure 6B:
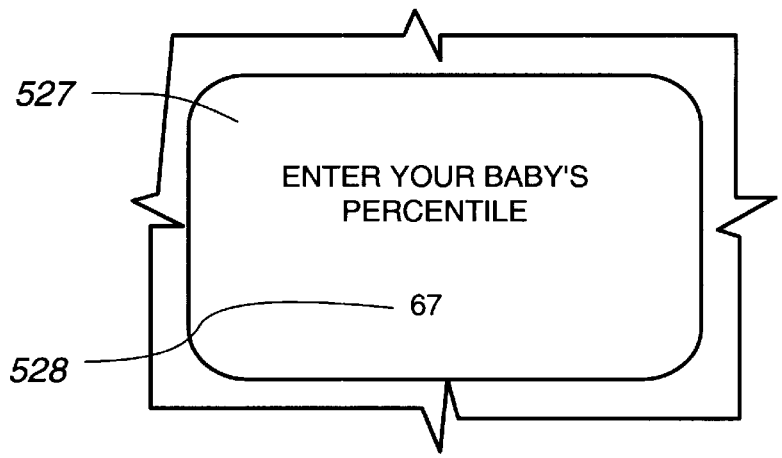
Figure 6C:
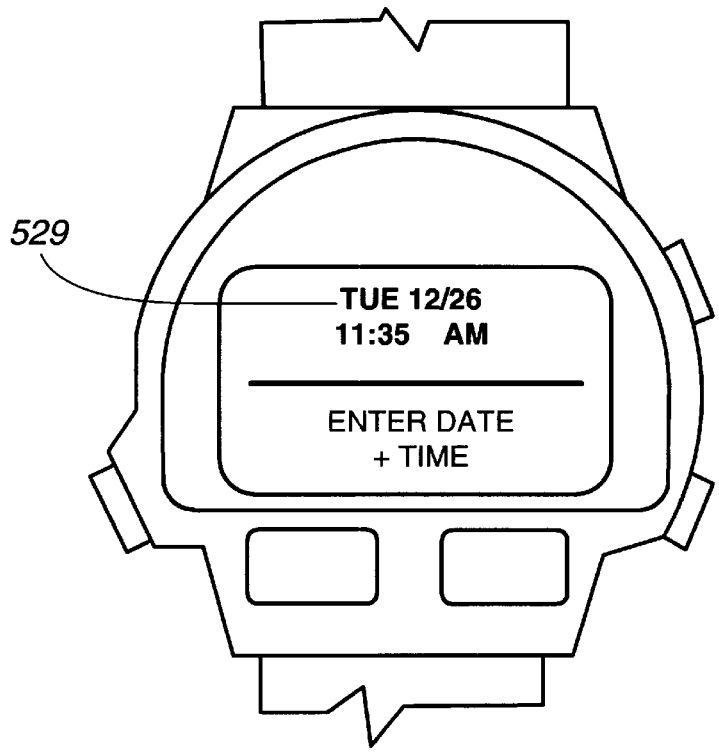

The Receive Data routine 450 executes Entry Screen routine 520 to create a display which tells the user to input pregnancy data. FIGS. 6a and 6b show exemplary data input screens.

Referring to FIGS. 6a and 6b, the data entry screens 525 and 527 request that the user enter the following pregnancy reference data: pregnancy reference date 526 and fetus percentile 528. The pregnancy reference date 526 may be entered in various forms, such as the expected due date 523 or the last menstrual period date 524. Alternatively, the pregnancy reference date may be entered as the conception date, or other dates that are related to the beginning of the pregnancy. The fetus percentile is the ratio of the size of the woman's fetus to a statistically average fetus. This percentile is used to customize the status of fetal development for the particular woman whose information is stored in the storage device 150.

If a dock is not available, the Entry Screen routine 520 may also include an entry screen for the current date and/or time. A completed date and time screen is shown as screen 529 in FIG. 6c.

Additionally, the pregnancy reference data requested may include other pregnancy related data, such as the sex of the fetus if known (not shown), the doctor's name and number (not shown), or the next scheduled doctor visit (not shown).

Referring again to FIG. 6a, in accordance with the preferred embodiment of the invention the user may enter either the expected due date 523 or the last menstrual period date 524 as the pregnancy reference date 526. This date is received by Receive Entry routine 530. Based on whether the date entered by the user is before or after the current date, the Data Type routine 540 will identify what type of pregnancy reference date was entered. If the date entered is before the current date, the entered date will be considered by the Data Type routine as the last menstrual period; otherwise the Data Type routine will consider the date as the expected due date.

Next, the Receive Data routine 450 executes test validity routine 550 to check whether the data entered is valid. The routine will base a determination of whether the pregnancy reference date 526 is valid upon the current date and a set maximum gestation period. If the period between the pregnancy reference date 526 and the current date is larger than the maximum gestation period, the program displays an error message (not shown), and requests that the user re-enter the pregnancy reference date. Where the embodiment of the invention provides pregnancy data for a human fetus, the maximum gestation period may be set to 308 days.

Once the user enters a valid pregnancy reference date 526, the Normalize routine 560 is executed. The Normalize routine 560 converts the pregnancy reference date 526 to the expected due date, and stores the expected date in the storage device. If the pregnancy reference date entered 526 is the date of the last menstrual period 524, the entered date is converted to the expected due date by adding to it the normal gestation period, according to the following formula:

$$\text{expected due date} = \text{last menstrual period date} + \text{normal gestation period}$$

For a human fetus, the normal gestation period is preferably set to 280 days. Subsequent data calculations are based on this expected due date. Alternatively, the pregnancy reference date may be stored as the last menstrual period date 524, and the fetal development output data calculations could be based on the last menstrual period date 524. Once this information is stored, it will be retrieved by the Retrieve Data routine 410 automatically each time Fetal mode 60 is requested until the user modifies the values.

Referring to FIG. 3, the Retrieve Data routine 410 retrieves and passes the available pregnancy reference data to the Determine Parameters routine 420. The Determine Parameters routine is shown in more detail in FIG. 7.

Figure 7:
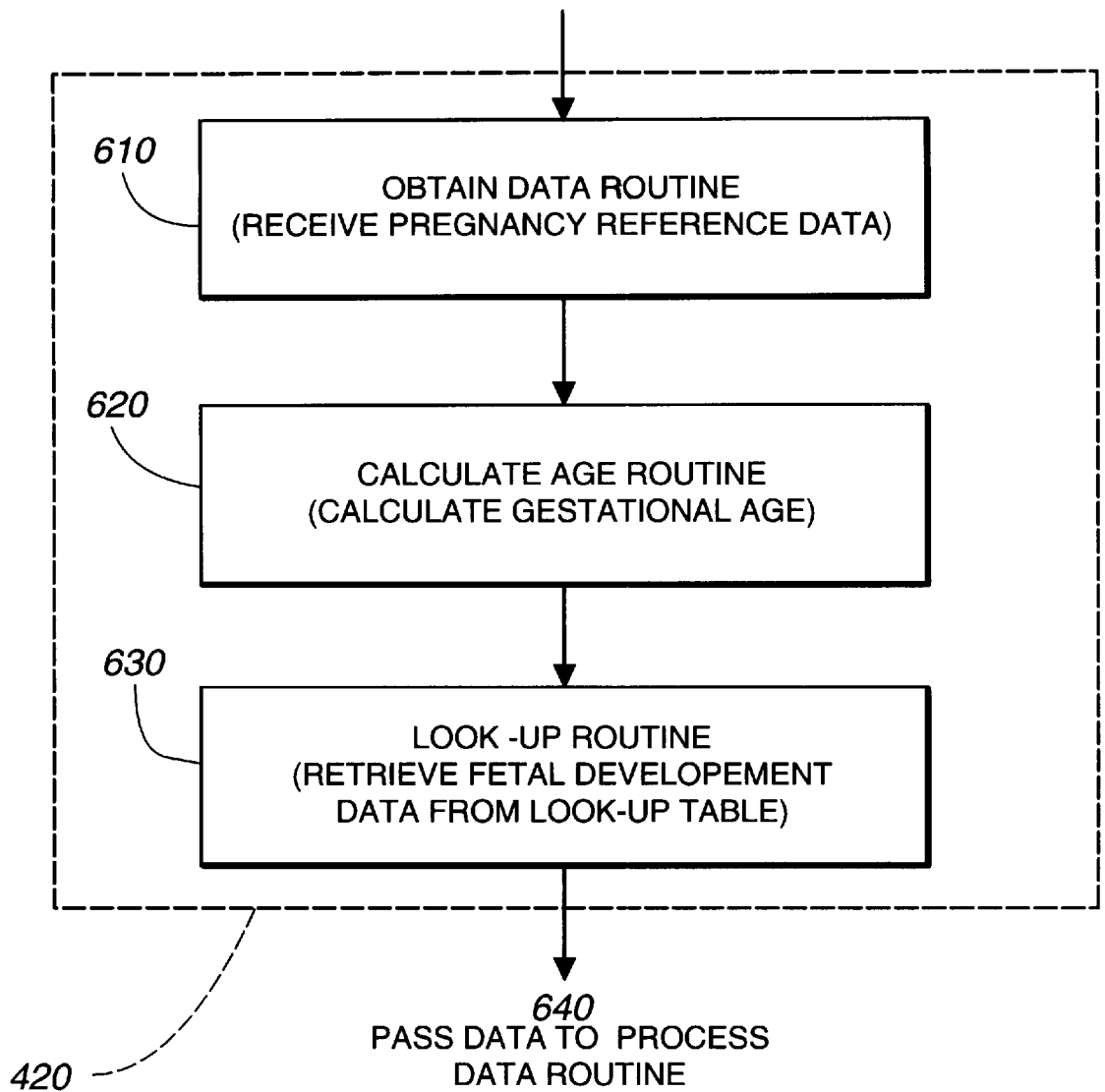
FIG. 7 shows a flowchart of a Determine Parameters software routine.

With reference to FIG. 7, the Determine Parameters routine 420 executes the Obtain Data routine 610 to receive the previously entered pregnancy reference data. In order to determine the relevant fetal development parameter data, a Calculate Age routine 620 is executed. The gestational age is based on the pregnancy reference date and the current date. Assuming that the pregnancy reference date is the expected due date, the gestational age is the difference in days between the sum of the gestation period and the current date, minus the expected due date, or mathematically:

$$\text{gestational age} = \text{current date} + \text{gestation period} - \text{expected due date}.$$

Within the look-up table 160, the fetal development parameter data is indexed to gestational ages. Using the computed gestational age as a reference, the Look-up routine 630 retrieves the matching fetal development data from the look-up table. The fetal development data is passed to the Process Data routine 430, at step 640.

FIG. 8 shows an example of the type of fetal development parameter data 710 that is stored in the look up table 160. The fetal development parameter data stored includes the statistical norm of a fetus' weight 720 and the statistical norm of a fetus' length 730 for each day 740 and week 750 of the gestational period, based on a maximum gestational period.

The fetal development parameter data may also include other pregnancy related event data, such as a pregnancy journal page reference 760. This page reference refers the user to the pages in a pregnancy journal textbook corresponding to the current stage of pregnancy. The pregnancy journal textbook may be sold in conjunction with the present invention or separately. Alternatively, the text of the pregnancy journal textbook may be stored in the storage device. In this alternative embodiment, the page references are addressed corresponding to the memory locations of the pregnancy journal text.

The fetal development parameter data may also include references to text messages stored either in the look-up table or separately. The sort messages provide the user with more information about the current status of fetal development. This additional information includes events which should occur during a particular stage of development, such as formation of feet, arms, eyes, lungs, etc.

After determining the pregnancy reference data and the retrieved fetal development parameter data, the Fetal mode 60 executes the Process Data routine 430, as shown in FIG. 3. The Process Data routine 430 estimates the current status of fetal development.

Specifically, the Process Data routine 430 determines the time to due date 820 (FIG. 9b) by computing the difference between the previously computed gestational age and the normal gestation period.

The Process Data routine 430 adjusts the statistical norm of the fetus' weight 720 and length 730 (FIG. 8) obtained from the look-up table by multiplying the numbers from the look-up table by the fetus' percentile 528 (FIG. 6b). The fetus percentile is the ratio of the size of the woman's fetus to a statistically average fetus. This results in an estimated weight and length that is customized for the individual woman. If the fetus' percentile 528 is not available, or has not been entered into the storage device 150, the statistical norm for the fetus' weight and length will be used as the fetus' weight and length. Additionally, the Process Data routine 430 may factor information regarding the fetus' sex into the final fetus weight and length calculation.

Figure 9A:
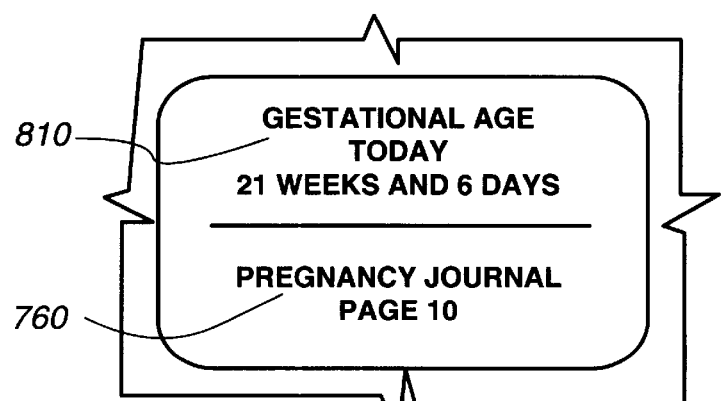
FIGS. 9a, 9b, 9c and 9d show exemplary output screens used to display the current status of fetal development.

Although the pregnancy journal page 760 is referenced in FIG. 9a, the Process Data routine 430 may alternatively locate and retrieve text messages corresponding to the pregnancy journal page reference, or other stored text.

The Process Data routine 430 passes the current status of fetal development to the Display Status routine 440 for display to the user.

Figure 9B:
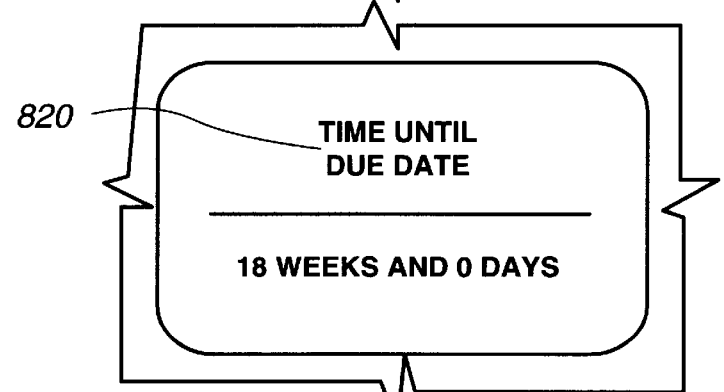
Figure 9C:
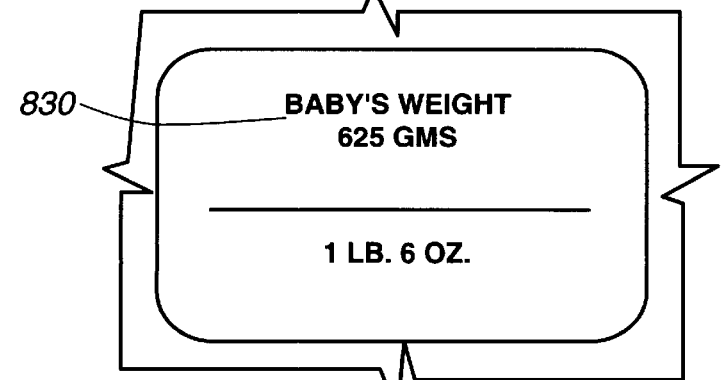
Figure 9D:
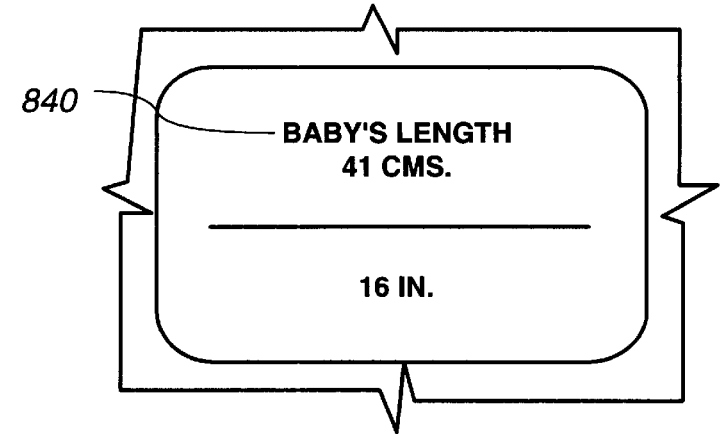

FIGS. 9a–9d depict exemplary display screens showing the current status of fetal development as calculated by Process Data routine 430. The current status of fetal development may include estimated gestational period measurements 810, 820 (FIGS. 9a and 9b), estimated fetal measurements 830, 840 (FIGS. 9c, 9d), and/or pregnancy related event data 760 (FIG. 9a). Gestation period measurements include the gestational age 810 and the time to due date 820, as shown in FIGS. 9a and 9b. Expected fetal measurements include the fetus' weight 830 and the fetus' length 840, as shown in FIGS. 9c and 9d. Pregnancy related event data includes other data such as the pregnancy journal page reference 760, as shown in FIG. 9a. The Process Data routine 430 calculates these values as using the fetal development parameter data and the pregnancy reference data.

Preferably, the output display screens showing the gestational age and time (FIGS. 9a and 9b) are displayed first, followed by the fetus' weight and length display screens (FIGS. 9c and 9d).

In the preferred embodiment, the final output display screen is followed by a Receive Data routine 450, so that the user may review and update the pregnancy reference data if desired. As sown in FIG. 1, the user may enter Receive Data mode 50 separately to review and update the pregnancy reference data. The Receive Data mode 50 calls the receive data to routine 450, as shown in FIG. 5.

In this manner, the user sees the current status of fetal development in the order of importance. The user will first see displays (FIGS. 9a–9d) concerning how far along the pregnancy is, followed by displays concerning the fetus length, and the fetus weight. Finally, the user is able to review the pregnancy reference data in the data entry screen displays (FIGS. 6a–6c), and modify the data if necessary.

In an alternative embodiment, the user can select which output screen she wishes to view at any one time. The user can then toggle to another output screen or return to Normal mode. If the user does not toggle back to the Normal mode screen within a certain period of time, the watch may automatically revert to Normal mode.

It is clear to those skilled in the art that many and varied modifications to the screen interface design and screen display design(s) are apparent to the artisan of ordinary skill in the art.

While this invention, as described herein, is primarily geared for use by pregnant women, it can be used by anyone wishing to learn information about the current stage of a fetus development. The invention may be used by expectant fathers or grandparents as well to help keep them informed about a baby's stage of development.

Alternatively, the invention may be used by breeders or veterinarians to obtain information about the fetal development stage of a specific animal.

It will be dear to those in the art that many and varied modifications are apparent to the artisan of ordinary skill. All such variations and modifications are intended to be within the scope of the appended claims.

I claim:

1. A watch apparatus allowing a user to readily and automatically determine the stage of development of a fetus, comprising:
    a watch case;
    a watch data entry mechanism, comprising a plurality of buttons disposed on the watch case, for entering and updating pregnancy reference data, a pregnancy reference date, and a fetus percentile;
    a processor, connected to the data entry mechanism and contained within the watch case;
    a storage device, connected to the processor and contained within the watch case, for storing fetal development parameter data, the pregnancy reference date, and the fetus percentile;
    a clock connected to the processor and disposed within the watch case, which outputs a current date; and
    a watch display screen, connected to the processor;
    wherein the processor, using the pregnancy reference date, the fetus percentile, and the current date, can repeatedly and automatically estimate a current status of fetal development, wherein the current status of fetal development comprises an estimate of a weight, length, and gestational age for the fetus as of the current date, and displays the current status of fetal development on the watch display screen, throughout gestation and without having to reenter any user modified pregnancy reference data.

2. The apparatus of claim 1, wherein
    the watch display screen is adapted for depicting the current status of fetal development as well as conventional watch data.

3. The apparatus of claim 1, wherein the processor comprises:
    means for processing the current status of fetal development, using the stored fetal development parameter data.

4. The apparatus of claim 1, wherein the current status of fetal development includes gestation period estimates corresponding to the current stage of pregnancy.

5. The apparatus of claim 1, wherein the current status of fetal development includes fetal measurement estimates corresponding to the current stage of pregnancy.

6. The apparatus of claim 1, wherein the current status of fetal development further includes pregnancy related event data corresponding to the current stage of pregnancy.

7. The apparatus of claim 1, wherein the storage means comprises:
    a look-up table containing standardized data regarding fetal measurements for a plurality of stages of development.

8. The apparatus of claim 1, wherein the storage device comprises:
    a look-up table containing pregnancy related event data for a plurality of stages of development.

9. The apparatus of claim 1, wherein an operating program controls a fetal information mode of operation, and wherein the fetal information mode of operation retrieves the pregnancy reference date and processes the current status of fetal development using the pregnancy reference date and the corresponding fetal development parameter data.

10. A method comprising the steps of:
    storing pregnancy reference data in a storage device, wherein the pregnancy reference data comprises a pregnancy reference date and a fetus percentile, the storage device contained within a watch case;
    retrieving pregnancy reference data from the storage device;
    determining relevant fetal development parameter data using the retrieved pregnancy reference data;
    repeatedly processing the pregnancy reference data and the fetal development parameter data throughout gestation and without having to reenter any user modified pregnancy reference data to obtain the current estimated status of fetal development, wherein the processing is performed by a processor disposed within the watch case; and
    repeatedly displaying the current estimated status of fetal development, wherein the current estimated status of fetal development comprises an estimate of a weight, length, and due date for a fetus, on a watch display screen throughout gestation, the watch display screen disposed within the watch case, wherein users can conveniently and automatically view the current estimated status of fetus development.

11. The method of claim 10, wherein the pregnancy reference data includes a pregnancy reference date, further comprising the steps of:
    identifying the type of pregnancy reference date; and
    normalizing the pregnancy reference date to a standard format.

12. The method of claim 13, further comprising the step of obtaining the current date from a clock.

13. The method of claim 10, wherein the determining step further comprises the steps of:
    calculating a gestational age using the pregnancy reference data; and
    accessing a look-up table to retrieve the relevant fetal development parameter data corresponding to the gestational age.

14. The method of claim 10, wherein the processing step further comprises the steps of:
    customizing the current estimated status of fetal development based upon a stored fetus percentile.

15. A computer based apparatus allowing a user to readily and automatically determine the stage of development of a fetus, comprising:
    a computer workstation, comprising;

a data entry mechanism for entering pregnancy reference data, a pregnancy reference date, and a fetus percentile;

a processor, operably connected to the data entry mechanism;

a storage device, connected to the processor for storing fetal development parameter data, the pregnancy reference date, the fetus percentile, and the pregnancy reference data, wherein the storage device contains a look-up table containing pregnancy related event data for a plurality of stages of development;

a clock, connected to the processor, which outputs the current date;

a display screen, connected to the processor;

wherein the processor, using the pregnancy reference data, the pregnancy reference date, the fetus percentile, and the current date, can repeatedly and automatically estimate a current status of fetal development, wherein the current status of fetal development comprises an estimate of a weight, length, and due date for the fetus, and displays the current status of fetal development on the display screen, throughout gestation and without having to reenter any user modified pregnancy reference data.

16. A method comprising the steps of:

storing pregnancy reference data in a storage device, wherein the pregnancy reference data comprises a pregnancy reference date and a fetus percentile, the storage device contained within a computer workstation;

retrieving pregnancy reference data from the storage device;

determining relevant fetal development parameter data using the retrieved pregnancy reference data;

repeatedly processing the pregnancy reference data and the fetal development parameter data to obtain the current estimated status of fetal development, wherein the processing is performed by a processor disposed within the computer workstation;

calculating a gestational age using the pregnancy reference data;

repeatedly accessing a look-up table, stored in the storage device, to retrieve an estimated weight and height, and the relevant fetal development parameter data corresponding to gestational age throughout gestation; and repeatedly displaying the current estimated status of fetal development on a display screen throughout gestation, wherein users can conveniently and automatically view the current estimated status of fetus development.

17. The method of claim 16, wherein the pregnancy reference data includes a pregnancy reference date, further comprising the steps of:

identifying the type of pregnancy reference date; and normalizing the pregnancy reference date to a standard format.

18. The method of claim 16, wherein the retrieving step further comprises the step of retrieving the current date from a clock.

19. The method of claim 16, wherein the processing step further comprises the step of customizing the current estimated status of fetal development based upon a stored fetus percentile.

* * * * *